United States Patent

Murabayashi et al.

[11] Patent Number: 6,037,495
[45] Date of Patent: *Mar. 14, 2000

[54] PROCESS FOR PRODUCING ALKOXYIMINOACETAMIDE DERIVATIVES

[75] Inventors: Akira Murabayashi, Ibaraki; Kazuo Ueda, Suzuka-gun; Akira Ino, Koka-gun, all of Japan

[73] Assignee: Shinonogi & Co., Ltd., Osaka, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/793,453

[22] PCT Filed: Aug. 30, 1995

[86] PCT No.: PCT/JP95/01716

§ 371 Date: Feb. 26, 1997

§ 102(e) Date: Feb. 26, 1997

[87] PCT Pub. No.: WO96/07635

PCT Pub. Date: Mar. 14, 1996

[30] Foreign Application Priority Data

Sep. 6, 1994 [JP] Japan ..................................... 6-212690
Dec. 6, 1994 [JP] Japan ..................................... 6-302050

[51] Int. Cl.⁷ ......................... C07C 233/05; C07C 231/08
[52] U.S. Cl. ........................................... 564/164; 564/163
[58] Field of Search ................................... 564/163, 164, 564/169; 562/843, 840

[56] References Cited

U.S. PATENT DOCUMENTS 5,387,714 2/1995 Takase et al. ........................... 562/843
5,442,063 8/1995 Takase et al. ........................... 544/333

FOREIGN PATENT DOCUMENTS 40 42 273 A1 7/1992 Denmark .
0 596 692 5/1994 European Pat. Off. .
5-97768 4/1993 Japan .
0629986 8/1994 Japan .
9307116 4/1993 WIPO .
95/34526 12/1995 WIPO .

*Primary Examiner*—Shailendra Kumar
*Attorney, Agent, or Firm*—Foley & Lardner

[57] ABSTRACT

A process for producing a compound of the formula (I):

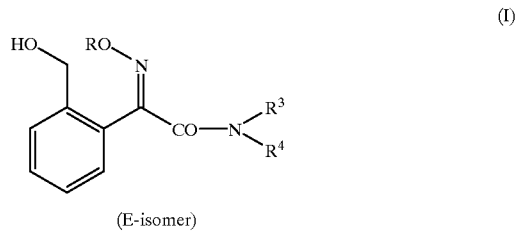

(E-isomer)

wherein R is hydrogen or an alkyl group, and $R^3$ and $R^4$ are hydrogen or an alkyl group, which comprises reacting a compound of the formula (II):

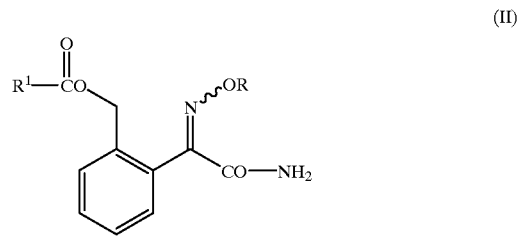

wherein $R^1$ is an optionally substituted alkyl group or an optionally substituted phenyl group, with a compound of the formula (III):

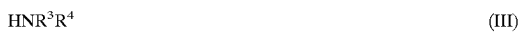

wherein each symbol is as defined above, and optionally alkylating the resulting compound. Intermediates for this process are also provided.

3 Claims, No Drawings

PROCESS FOR PRODUCING ALKOXYIMINOACETAMIDE DERIVATIVES

This application is a 371 of PCT/JP95/01716, filed Aug. 30, 1995.

TECHNICAL FIELD

The present invention relates to a process for producing an alkoxy(or hydroxy)iminoacetamide derivative and to intermediates for the production. Specifically, the present invention relates to a process for producing a 2-(2-hydroxymethylphenyl)-2-alkoxy(or hydroxy) iminoacetamide derivative useful as an intermediate for the production of alkoxyiminoacetamide compounds having potent fungicidal activity, and to intermediates for the production.

BACKGROUND OF THE INVENTION 2-(2-Hydroxymethylphenyl)-2-alkoxy(or hydroxy) iminoacetamide derivative is useful as an intermediate for the production of alkoxyiminoacetamide compounds useful as agricultural fungicides (JP-A 3-246268, JP-A 4-182461), and various processes for producing it have been known (JP-A 3-246268, JP-A 5-097768). However, there is still a room for improvement of these methods, and it has been desired to develop superior industrial processes for the production.

The object of the present invention is to provide a safe and industrially advantageous process for producing an intermediate for the production of alkoxyiminoacetamide compounds useful as agricultural fungicides and also to provide intermediates for the production.

DISCLOSURE OF THE INVENTION

The present inventors have intensively studied to achieve the above object. As a result, it has been found that the reaction of 2-(2-acyloxymethylphenyl)-2-alkoxy(or hydroxy)iminoacetamide with an amine is an industrially advantageous process for producing a 2-(2-hydroxymethylphenyl)-2-alkoxy(or hydroxy) iminoacetamide derivative useful as an intermediate for the production of alkoxyiminoacetamide compounds. After further studies based on this finding, the present invention has been completed.

That is, the present invention relates to:

(1) A process for producing a compound of the formula (I):

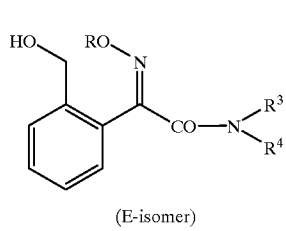

(E-isomer)

wherein R is hydrogen or an alkyl group, and $R^3$ and $R^4$ are the same or different and are hydrogen or an alkyl group, which comprises reacting a compound of the formula (II):

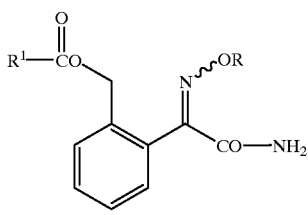

wherein $R^1$ is an optionally substituted alkyl group or an optionally substituted phenyl group, ~ indicates any configuration of an E-isomer, a Z-isomer and a mixture thereof, and the other symbols are as defined above, with a compound of the formula (III):

$$HNR^3R^4 \quad (III)$$

wherein each symbol is as defined above;

(2) A process for producing a compound of the formula (I-2):

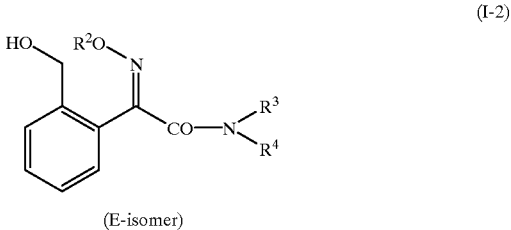

(E-isomer)

wherein $R^2$ is an alkyl group, and $R^3$ and $R^4$ are the same or different and are hydrogen or an alkyl group, which comprises reacting a compound of the formula (II-1):

wherein $R^1$ is an optionally substituted alkyl group or an optionally substituted phenyl group, ~ indicates any configuration of an E-isomer, a Z-isomer and a mixture thereof, and the other symbols are as defined above, with a compound of the formula (III):

$$HNR^3R^4 \quad (III)$$

wherein each symbol is as defined above to obtain a compound of the formula (I-1):

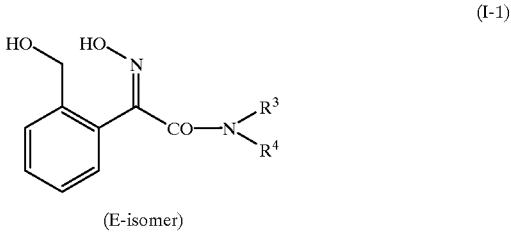

(E-isomer)

wherein each symbol is as defined above, and then alkylating the compound of the formula (I-1);

(3) A process for producing a compound of the formula (I-2):

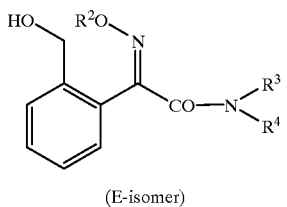

(E-isomer)

wherein $R^2$ is an alkyl group, and $R^3$ and $R^4$ are the same or different and are hydrogen or an alkyl group, which comprises alkylating a compound of the formula (II-1):

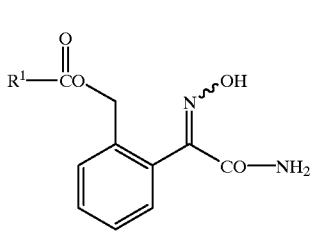

wherein $R^1$ is an optionally substituted alkyl group or an optionally substituted phenyl group, ~ indicates any configuration of an E-isomer, a Z-isomer and a mixture thereof, and the other symbols are as defined above, to obtain a compound of the formula (II-2):

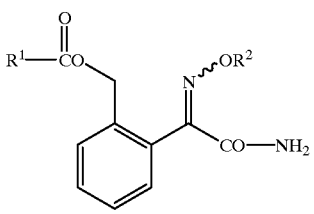

wherein each symbol is as defined above, and then reacting the compound of the formula (II-2) with a compound of the formula (III):

    (III)

wherein each symbol is as defined above;

(4) The process according to above item (1), wherein the compound of the formula (II) is obtained by reacting a compound of the formula (VI):

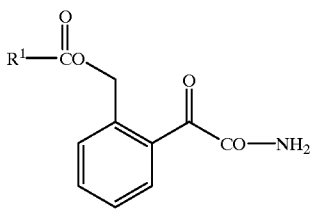

wherein $R^1$ is as defined in above item (1), with a compound of the formula (V):

$NH_2OR$    (V)

wherein R is as defined in above item (1) and/or a salt thereof;

(5) The process according to above item (2), wherein the compound of the formula (II-1) is obtained by reacting a compound of the formula (VI) with hydroxylamine and/or a salt thereof;

(6) The process according to above item (3), wherein the compound of the formula (II-1) is obtained by reacting a compound of the formula (VI) with hydroxylamine and/or a salt thereof;

(7) The process according to any one of above items 4 to 6, wherein the compound of the formula (VI) is obtained by introducing a benzoyloxy group (in which the phenyl group may optionally be substituted) or an alkanoyloxy group (in which the alkyl group may optionally be substituted) into a compound of the formula (VII):

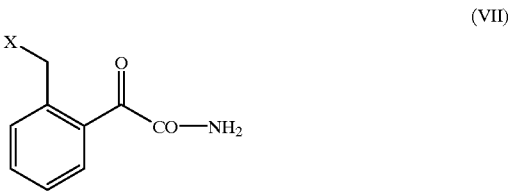

wherein X is halogen;

(8) The process according to above item (7), wherein a compound of the formula (VII) is reacted with a metal salt of a carboxylic acid of the formula (XIII):

$R^1COOH$    (XIII)

wherein $R^1$ is as defined in claim 1, or is reacted with a carboxylic acid of the formula (XIII) in the presence of a base;

(9) The process according to any one of above items (1) to (3), wherein $R^1$ is a methyl group;

(10) The process according to any one of above items (1) to (3), wherein at least one of $R^3$ and $R^4$ is an alkyl group;

(11) A compound of the formula (I-1'):

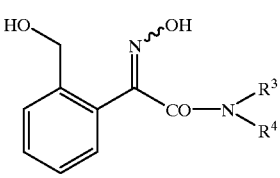

wherein $R^3$ and $R^4$ are the same or different and are hydrogen or an alkyl group, and ~ indicates any configuration of an E-isomer, a Z-isomer or a mixture thereof, or a salt thereof;

(12) A compound of the formula (II-1):

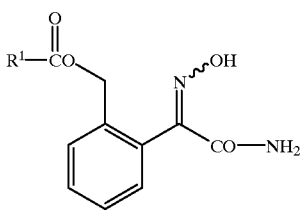

(II-1)

wherein R¹ an optionally substituted alkyl group or an optionally substituted phenyl group, and ~ indicates any configuration of an E-isomer, a Z-isomer and a mixture thereof, or a salt thereof;

(13) A compound of the formula (VI):

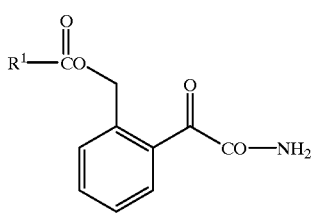

(VI)

wherein R¹ is an optionally substituted alkyl group or an optionally substituted phenyl group; and

(14) A compound of the formula (VII):

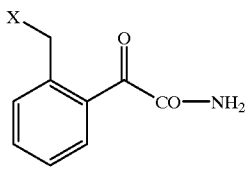

(VII)

wherein X is halogen.

The alkyl groups of the optionally substituted alkyl groups represented by $R^1$ include, for example, alkyl groups having 1 to 8 carbon atoms, preferably 1 to 6 carbon atoms. Examples of the alkyl groups are methyl, ethyl, propyl, isopropyl, butyl, isobutyl, sec-butyl, t-butyl, etc. In particular, methyl is preferred.

The substituted alkyl groups include, for example, haloalkyl groups having as the substituent(s) at least one halogen atom (e.g., fluorine, chlorine, bromine, iodine) (e.g., difluoromethyl, trifluoromethyl, chloromethyl, 2-bromoethyl, 2,3-dichloropropyl, etc.); alkoxyalkyl groups having as the substituent(s) at least one alkoxy group having 1 to 8 carbon atoms, preferably 1 to 4 carbon atoms (e.g., methoxy, ethoxy, propoxy, butoxy, etc.) (e.g., methoxymethyl, ethoxymethyl, methoxyethyl, etc.); phenylalkyl groups having optionally substituted phenyl as the substituent(s) (e.g., benzyl, etc.), etc. The substituents of the phenyl group of the phenylalkyl groups include, for example, lower alkyl groups (wherein the term "lower" means $C_{1-8}$, preferably $C_{1-6}$, more preferably $C_{1-4}$; the term "lower" has the same meaning with respect to other groups described below) (e.g., methyl, ethyl, propyl, butyl, etc.), lower alkenyl groups (e.g., vinyl, allyl, crotyl, etc.), lower alkynyl groups (e.g., ethynyl, propargyl, butynyl, etc.), cycloalkyl groups (e.g., cyclopropyl, cyclopentyl, cyclohexyl, etc.), cycloalkenyl groups (e.g., cyclopentenyl, cyclohexenyl, etc.), lower alkanoyl groups (e.g., acetyl, propionyl, isobutyryl, etc.), lower alkylsilyl groups (e.g., methylsilyl, ethylsilyl, propylsilyl, butylsilyl, etc.), halo(lower)alkyl groups (e.g., trifluoromethyl, chloromethyl, 2-bromoethyl, 1,2-dichloropropyl, etc.), amino, mono(lower)alkylamino groups (e.g., methylamino, ethylamino, etc.), di(lower)alkylamino groups (e.g., dimethylamino, diethylamino, etc.), phenyl, phenyl(lower)alkyl groups (e.g., benzyl, phenethyl, etc.), phenyl(lower)alkenyl groups (e.g., styryl, cinnamyl, etc.), furyl(lower)alkyl groups (e.g., 3-furylmethyl, 2-furylethyl, etc.), furyl(lower)alkenyl groups (e.g., 3-furylvinyl, 2-furylallyl, etc.), halogen atoms (e.g., fluorine, chlorine, bromine, iodine), a nitro group, a cyano group, a carboxyl group, —COOR' (wherein R' is a lower alkyl group as defined above), —OR⁵ [wherein R⁵ is a hydrogen atom, a lower alkyl group (e.g., methyl, ethyl, propyl, etc.), a lower alkenyl group (e.g., vinyl, allyl, crotyl, etc.), a lower alkynyl group (e.g., ethynyl, 2-propynyl, 3-butynyl, etc.), a lower alkanoyl group (e.g., acetyl, propionyl, butyryl, etc.), a phenyl group, a lower alkoxyphenyl group (e.g., 3-methoxyphenyl, 4-ethoxyphenyl, etc.), a nitrophenyl group (e.g., 3-nitrophenyl, 4-nitrophenyl, etc.), phenyl(lower)alkyl groups (e.g., benzyl, phenethyl, phenylpropyl, etc.), cyanophenyl(lower)alkyl groups (e.g., 3-cyanophenylmethyl, 4-cyanophenylethyl, etc.), a benzoyl group, a tetrahydropyranyl group, a pyridyl group, a trifluoromethylpyridyl group, a pyrimidinyl group, a benzothiazolyl group, a quinolyl group, benzoyl(lower)alkyl groups (e.g., benzoylmethyl, benzoylethyl, etc.), a benzenesulfonyl group, or lower alkylbenzenesulfonyl groups (e.g., toluenesulfonyl, etc.)], —CH₂—Z—R⁶ [wherein Z is —O—, —S—, or —NR⁷— (in which R⁷ is a hydrogen atom or a lower alkyl group), R⁶ is a phenyl group, a halophenyl group (e.g., 2-chlorophenyl, 4-fluorophenyl, etc.), a lower alkoxy phenyl group (e.g., 2-methoxyphenyl, 4-ethoxyphenyl, etc.), a pyridyl group, or a pyrimidinyl group], etc.

The optionally substituted phenyl group represented by R¹ include unsubstituted and substituted phenyl groups.

The substituents of the substituted phenyl groups include alkyl groups, alkoxy groups, halogen atoms, halogenated alkyl groups, etc. The alkyl groups include, for example, alkyl groups having 1 to 8 carbon atoms, preferably 1 to 6 carbon atoms, such as methyl, ethyl propyl, isopropyl, butyl, isobutyl, sec-butyl, t-butyl, etc. The alkoxy groups include, for example, alkoxy groups having 1 to 8 carbon atoms, preferably 1 to 4 carbon atoms, such as methoxy, ethoxy, propoxy, butoxy, etc. The halogen atoms include, for example, fluorine, chlorine, bromine and iodine. The halogenated alkyl groups include alkyl groups as defined above each of which is substituted by at least one halogen atom. Examples of the halogenated alkyl groups include difluoromethyl, trifluoromethyl, chloromethyl, 2-bromoethyl, 2,3-dichloropropyl, etc.

Of these substituents, a methyl group, a methoxy group, a chlorine atom, etc., are preferred.

These substituents may be at any possible position on the phenyl group. The number of the substituent(s) is 1 to 3, preferably 1 to 2.

R¹ is preferably an alkyl group, more preferably methyl.

The alkyl groups represented by R, R², R³ and R⁴ include alkyl groups having 1 to 8 carbon atoms, preferably 1 to 6 carbon atoms, such as methyl, ethyl, propyl, isopropyl, butyl, isobutyl, sec-butyl, t-butyl, etc. In particular, methyl is preferred for R and R². It is preferred that at least one of $R^3$ and $R^4$ is an alkyl group, preferably methyl. It is also preferred that both $R^3$ and $R^4$ are hydrogen.

The halogen represented by X includes, for example, fluorine, chlorine, bromine, and iodine.

The compounds represented by the formulas (I-I'), (II), (II-1) and (II-2) exist as E- and Z-isomers. Unless otherwise indicated, these compounds include their E- and Z-isomers, and mixtures thereof. This is indicated by the wave line (~) in the above formulas.

The compound of the formula (I-1') is preferably its E-isomer, i.e. the compound of the formula (I-1).

The compounds of the formula (I-1), (I-1') and (II-1), and the compound of the formula (IV) in the scheme below may be in the form of salts. Examples of the salts include alkaline metal salts (e.g., sodium salt, potassium salt, lithium salt, etc.), etc.

Preferred examples of the compounds of the formula (I) are compounds of the formula (I) wherein R is a hydrogen atom or methyl, and $R^3$ and $R^4$ are each a hydrogen atom;

R is a hydrogen atom or methyl, $R^3$ is a hydrogen atom, and $R^4$ is a methyl group; or R is a hydrogen atom or methyl, $R^3$ is methyl, and $R^4$ is a hydrogen atom.

Preferred embodiments of the processes of the invention are as follows.

The desired compounds of the formula (I) (hereinafter sometimes abbreviated as compound (I); compound of other formulas are likewise abbreviated) consist of the compound (I-1) which is a compound of the formula (I) wherein R is a hydrogen atom, and the compound (I-2) which is a compound of the formula (I) wherein R is an alkyl group. The compound (I-1), its Z-isomer and mixtures thereof (i.e. the compound (I-1) can be prepared according to Scheme 1, and the compound (I-2) can be prepared according to Scheme 3 or 4.

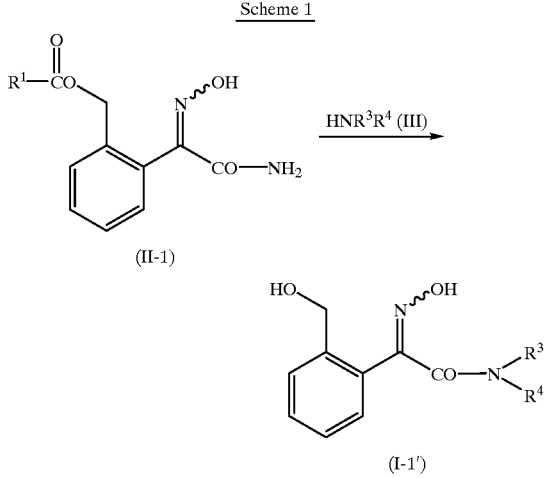

wherein each symbol is as defined above.

The compound (I-1') can be prepared by reacting the compound (II-1) with the compound (III) in an appropriate solvent under atmospheric pressure or in a sealed tube.

Examples of the compound (III) include methylamine, ethylamine, propylamine, dimethylamine, diethylamine, etc.

The amount of the compound (III) to be used is 1 to 50 mol, preferably 1 to 20 mol, per mol of the compound (II-1).

The solvent include, for example, alcohols (e.g., methanol, ethanol, propanol, etc.), water, ethers (e.g., ether, tetrahydrofuran (THF), dioxane, etc.), halogenated hydrocarbons (e.g., dichloromethane, 1,2-dichloroethane, chloroform, carbon tetrachloride, etc.), amides (e.g., N,N-dimethylformamide, etc.), hydrocarbons (e.g., benzene, toluene, xylene, etc.), nitrites (e.g., acetonitrile, etc.), etc. These solvents can be used alone or as mixtures thereof. In particular, alcohols are preferred.

The reaction temperature is normally 0 to 80° C., preferably 10 to 60° C., and the reaction time is normally 1 to 24 hours.

The compound (I-1') or the compound (I-1) thus obtained can be used in the next step as the reaction mixture or crude product, or after purifying it by conventional methods (e.g., chromatography, recrystallization, etc.).

This reaction can produce a high content of the E-isomer of the compound (I-1') (i.e. the compound (I-1), which is a preferred compound in the invention) even if the E/Z ratio of the starting compound (II-1) is low. Therefore it is not necessary that the E/Z ratio of the starting compound (II-1) should be high. If desired, however, the compound (II-1) may be isomerized to its E-isomer (i.e. the compound (IV)) according to Scheme 2 below for use in this reaction.

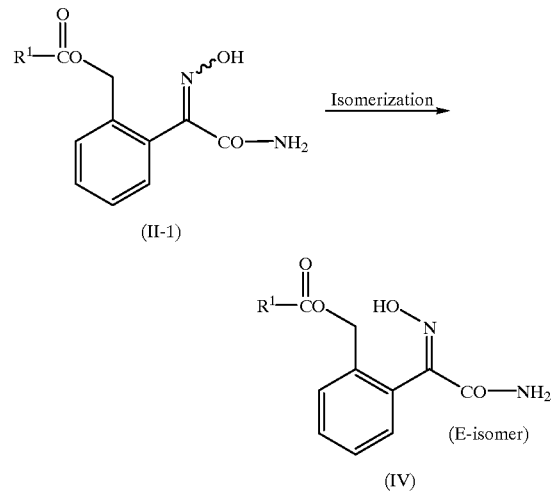

wherein each symbol is as defined above.

That is, the compound (II-1) can be isomerized to its E-isomer (i.e. the compound (IV)) in an appropriate solvent. The isomerization can normally be carried out by treating the compound (II-1) with an acid.

The acids include, for example, inorganic acids such as hydrochloric acid, sulfuric acid, phosphoric acid, etc., organic acids such as toluenesulfonic acid, etc. The amount of the acid to be used is 0.1 to 50 mol, preferably 1 to 20 mol, per mol of the compound (II-1).

The solvents include, for example, hydrocarbons (e.g., toluene, benzene, hexane, cyclohexane, etc.), halogenated hydrocarbons (e.g., dichloromethane, 1,2-dichloroethane, etc.), ketones (e.g., acetone, ethyl methyl ketone, etc.), alcohols (e.g., methanol, ethanol, etc.), ethers (e.g., ether, dioxane, etc.), etc. These solvents can be used alone or as mixtures thereof.

The reaction temperature is normally 0 to 100° C., preferably 10 to 60° C., and the reaction time is normally 0.5 to 24 hours.

The compound (IV) thus obtained can be used in the next step as the reaction mixture or crude product, or after purifying it by conventional methods (e.g., chromatography, recrystallization, etc.).

The compound (I-2) can be prepared according to Scheme 3 below.

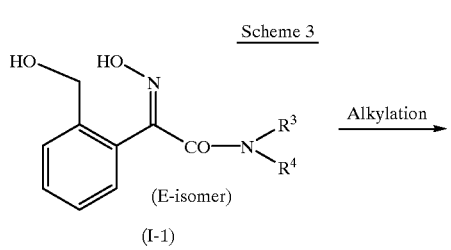

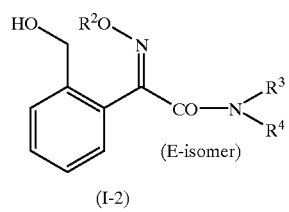

wherein each symbol is as defined above.

That is, the compound (I-2) can be prepared by alkylation by reacting the compound (I-1) with an alkylating agent in an appropriate solvent in the presence of a base.

The alkylating agents include, for example, dialkyl sulfate (e.g., di-$C_{1-6}$ alkyl sulfates such as dimethyl sulfate, diethyl sulfate, etc.), alkyl halides (e.g., $C_{1-6}$ alkyl halides such as methyl bromide, methyl iodide, etc.), etc. The amount of the alkylating agent to be used is 1 to 10 mol, preferably 1 to 1.5 mol, per mol of the compound (I-1).

The solvents include, for example, ketones (e.g., acetone, ethyl methyl ketone, etc.), ethers (e.g., tetrahydofuran, dioxane, etc.), hydrocarbons (e.g., toluene, benzene, hexane, cyclohexane, etc.), halogenated hydrocarbons (e.g., dichloromethane, etc.), alcohols (e.g., methanol, ethanol, etc.), water, etc. These solvents can be used alone or as mixtures thereof.

The bases include, for example, metal bicarbonates (e.g., sodium bicarbonate, potassium bicarbonate, etc.), metal carbonates (e.g., sodium carbonate, potassium carbonate, etc.), metal hydroxides (e.g., sodium hydroxide, potassium hydroxide, lithium hydroxide, etc.), metal hydrides (e.g., sodium hydride, lithium hydride, etc.), etc. The amount of the base to be used is 1 to 10 mol, preferably 1 to 2 mol, per mol of the compound (I-1).

If necessary, this reaction may be carried out in the presence of a phase-transfer catalyst. The phase-transfer catalysts include, for example, quaternary ammonium salts [e.g., tetraalkylammonium halides (e.g., tetrabutylammonium chloride, tetrabutylammonium bromide, etc.), tetraalkylammonium hydrosulfates (e.g., tetrabutylammonium hydrosulfate, etc.)], amines (e.g., tris(3,6-dioxaheptyl) amine, etc.), etc. The amount of the phase-transfer catalyst to be used is 0.01 to 1 mol, preferably 0.01 to 0.2 mol, per mol of the compound (I-1).

The reaction temperature is normally −20 to 100° C., preferably 0 to 50° C., and the reaction time is normally 1 to 24 hours.

The compound (I-2) thus obtained can be purified by conventional methods (e.g., chromatography, recrystallization, etc.).

The compound (I-2) can also be prepared according to Scheme 4 below.

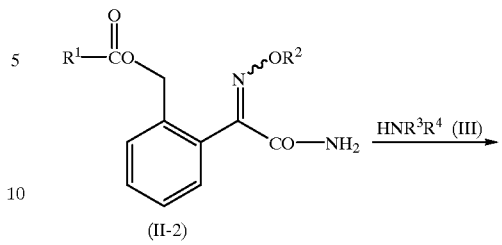

wherein each symbol is as defined above.

That is, the compound (I-2) can be prepared by reacting the compound (II-2) with the compound (III) in an appropriate solvent under atmospheric pressure or in a sealed tube.

This reaction can be carried out in the same manner as that described for the reaction of Scheme 1.

This reaction can produce a high content of the E-isomer of the compound (I-2), which is a preferred compound in the invention, even if the E/Z ratio of the starting compound (II-2) is low. Therefore it is not necessary that the E/Z ratio of the starting compound (II-2) should be high. If desired, however, the compound (II-2) may be isomerized to its E-isomer (i.e. the compound (II-2')) by the reaction of Scheme 5 below for use in this reaction.

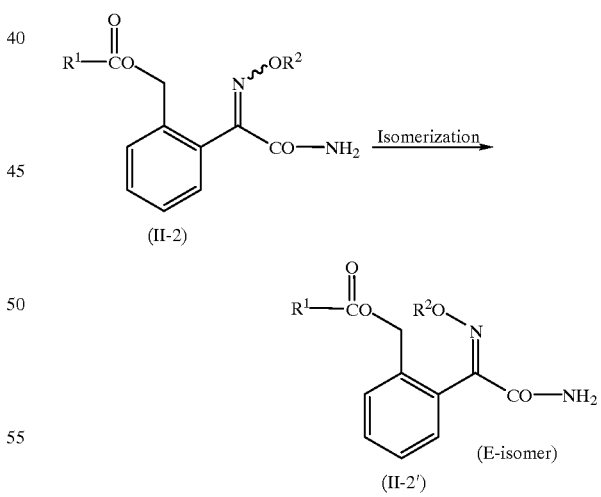

wherein each symbol is as defined above.

That is, the compound (II-2) can be isomerized to its E-isomer (i.e. the compound (II-2')) in an appropriate solvent. The isomerization can be carried out in the same manner as that described for the reaction of Scheme 2.

The compound (II-2) that can be used as the starting compound in the reactions of Schemes 4 and 5 can preferably be prepared according to Scheme 6 below.

Scheme 6

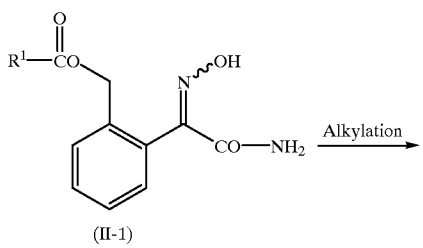

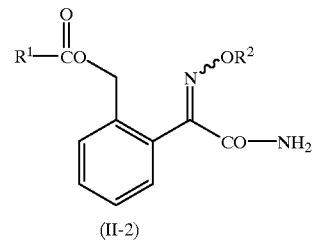

wherein each symbol is as defined above.

That is, the compound (II-2) can be prepared by alkylation by reacting the compound (II-1) with an alkylating agent in an appropriate solvent in the presence of a base. The alkylation can be carried out in the same manner as that described for the reaction of Scheme 3.

If desired, this alkylation may be carried out after isomerizing the starting compound (II-1) to its E-isomer.

Scheme 7

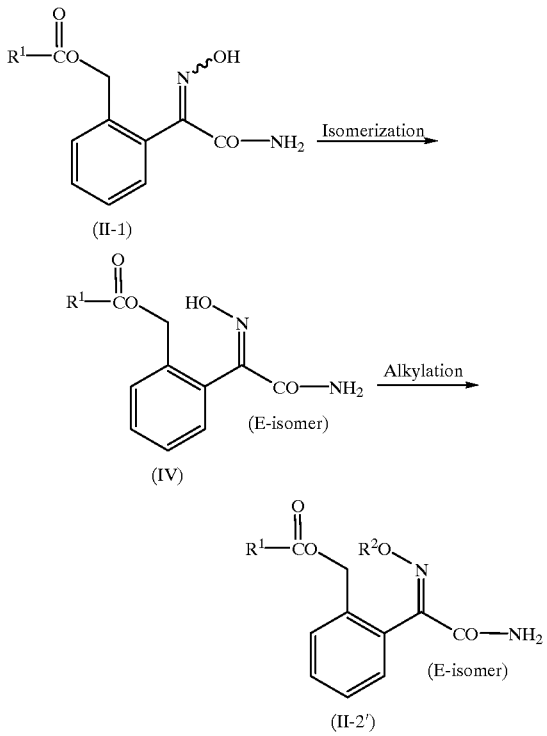

wherein each symbol is as defined above.

The isomerization to the E-isomer can be carried out in the same manner as that described for the reaction of Scheme 2. The alkylation can be carried out in the same manner as that described for the reaction of Scheme 6.

The compound (IV) and the compound (II-2') obtained in these reactions can be used in the next step as the reaction mixture or crude produce, or after purifying them by conventional methods (e.g., chromatography, recrystallization, etc.).

The compound (II-2') thus obtained can be used as the starting compound for the reaction of Scheme 4.

The compound (II-1) that can be used as the starting compound for the reactions of Schemes 1, 2, 6 and 7 can preferably be prepared according to Scheme 8.

Scheme 8

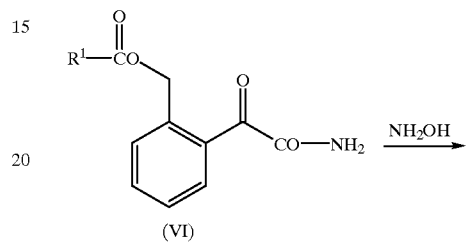

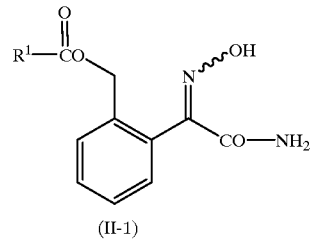

wherein each symbol is as defined above.

That is, the compound (II-1) can be obtained by reacting the compound (IV) with hydroxylamine and/or a salt thereof in an appropriate solvent.

The amount of hydroxylamine to be used is 1 to 5 mol, preferably 1 to 1.5 mol, per mol of the compound (IV).

The solvents include, for example, alcohols (e.g., methanol, ethanol, propanol, etc.), ethers (e.g., tetrahydrofuran, dioxane, etc.), hydrocarbons (e.g., toluene, benzene, hexane, etc.), water, etc. These solvents can be used alone or as mixtures thereof.

The salts of hydroxylamine include mineral acid salts (e.g., hydrochloric acid salts, sulfuric acid salts, etc.). When the salts are used, bases such as metal carboxylates (e.g., potassium acetate, sodium acetate, etc.), amines (e.g., pyridine, triethylamine, etc.), etc., may be used as acid condensing agents. The amount of the base to be used is 1 to 20 mol, preferably 1 to 10 mol, per mol of the hydroxylamine mineral acid salt.

The reaction temperature is normally 0 to 150° C., preferably 20 to 100° C., and the reaction time is normally 0.5 to 24 hours.

The compound (II-1) thus obtained can be used in the next step as the reaction mixture or crude product, or after purifying it by conventional methods (e.g., chromatography, recrystallization, etc.).

The compound (II-2) that can be used as the starting compound for the reactions of Scheme 4 and 5 can preferably be prepared according to Scheme 9.

Scheme 9

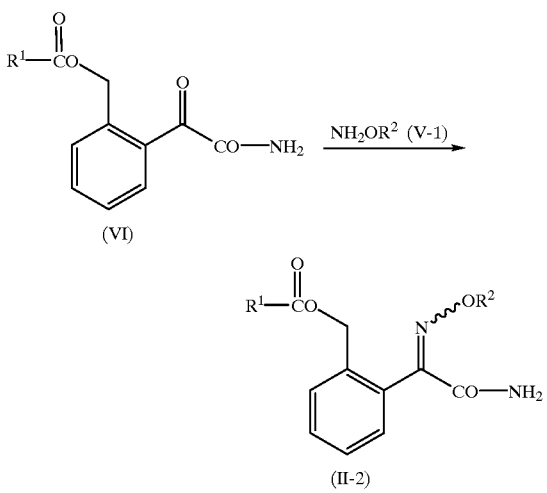

wherein each symbol is as defined above.

The compound (II-2) can be prepared by reacting the compound (VI) with the compound (V-1) and/or a salt thereof in an appropriate solvent. Examples of the compound (V-1) include methoxylamine, ethoxylamine, propyloxyamine, isopropyloxyamine, etc. The same salts as those of hydroxylamine in Scheme 8 can be used as the salts of the compound (V-1).

This reaction can be carried out in the same manner as that described for the reaction of Scheme 8.

The compound (VI) that can be used as the starting compound for the reactions of Schemes 8 and 9 can preferably be prepared according to Scheme 10.

Scheme 10

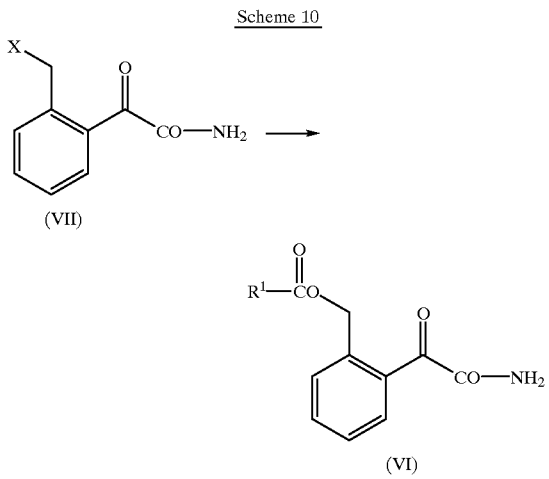

wherein each symbol is as defined above.

That is, the compound (VI) can be prepared by introducing a benzoyloxy group (in which the phenyl group may optionally be substituted) or an alkanoyloxy group (in which the alkyl group may optionally be substituted) into the compound (VII) in an appropriate solvent.

The introduction of the benzoyloxy or alkanoyloxy group can be carried out by reacting the compound (VII) with a metal salt (e.g., alkaline metal salts such as lithium salt, sodium salt, potassium salt; alkaline earth metal salts such as magnesium salt, calcium salt, etc.) of a carboxylic acid of, for example, the formula (XIII):

$$R^1COOH \quad (XIII)$$

wherein $R^1$ is as defined above, or reacting the compound (VII) with the carboxylic acid in the presence of a base. The metal salt of the carboxylic acid is preferably potassium acetate, or sodium acetate. The amount of the metal salt of the carboxylic acid or the carboxylic acid to be used is 1 to 10 mol, preferably 1 to 2 mol, per mol of the compound (VII).

The bases include, for example, metal hydroxides (e.g., sodium hydroxide, potassium hydroxide, lithium hydroxide, etc.), metal hydrides (e.g., sodium hydride, lithium hydride, etc.), metal carbonates (e.g., sodium carbonate, potassium carbonate, etc.), metal bicarbonates (e.g., sodium bicarbonate, potassium bicarbonate, etc.), etc.

The amount of the base to be used is not less than 1 mol, preferably 1.0 to 1.5 mol, per mol of the carboxylic acid (XIII).

This reaction is preferably carried out in the presence of a catalytic amount of a compound of the formula: MY wherein M is an alkaline metal (e.g., lithium, sodium, potassium, etc.) or an alkaline earth metal (e.g., magnesium, calcium, etc.) and Y is halogen (e.g., fluorine, chlorine, bromine, iodine) because the presence of the compound of the formula: MY increases the yield of the compound (VI). The amount of the compound of the formula: MY to be used is 0.01 to 1 mol, preferably 0.01 to 0.2 mol, per mol of the compound (VII). The compound of the formula: MY is preferably potassium iodide or sodium iodide.

The solvents include, for example, amides (e.g., N,N-dimethylformamide (DMF), etc.), ethers (e.g., dioxane, etc.), nitrites (e.g., acetonitrile, etc.), ketones (e.g., acetone, etc.), hydrocarbons (e.g., toluene, etc.), etc. These solvents can be used alone or as mixtures thereof. In particular, acetone or DMF is preferred.

The reaction temperature is normally 0 to 120° C., preferably 20 to 60° C., and the reaction time is normally 30 minutes to 20 hours.

The compound (VI) thus obtained can be used in the next step as the reaction mixture or crude product, or after purifying it by conventional methods (e.g., chromatography, recrystallization, etc.).

The compound (VII) that can be used as the starting compound for this reaction can preferably be prepared according to Scheme 11 below.

Scheme 11

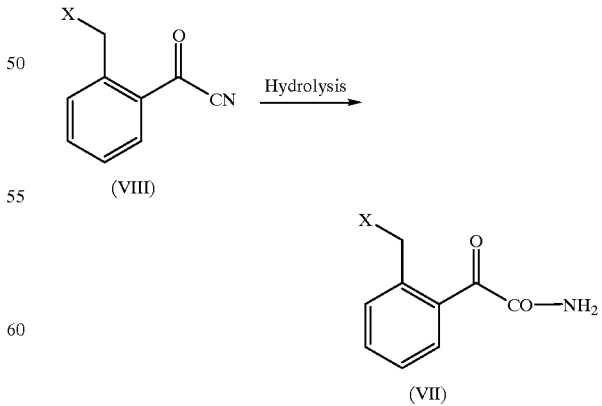

wherein each symbol is as defined above.

That is, the compound (VII) can be prepared by subjecting the compound (VIII) to hydrolysis in an appropriate solvent.

This hydrolysis can normally be carried out in the presence of an acid (see W. Wenner, Org. Synth. IV, 760 (1963)). The acids include, for example, inorganic acids such as hydrochloric acid, sulfuric acid, etc., organic acids such as p-toluenesulfonic acid, etc. The amount of the acid to be used is 1 to 50 mol, preferably 5 to 20 mol, per mol of the compound (VIII).

The solvents include water, ethers (e.g., dioxane, ether, etc.), etc. These solvents can be used alone or as mixtures thereof. In particular, water or dioxane is preferred.

The reaction temperature is normally 0 to 120° C., preferably 20 to 50° C., and the reaction time is normally 12 hours to 5 days.

The compound (VII) thus obtained can be used in the next step as the reaction mixture or crude product, or after purifying it by conventional methods (e.g., chromatography, recrystallization, etc.).

The compound (VIII) that can be used as the starting compound for this reaction can preferably be prepared according to Scheme 12 below.

Scheme 12

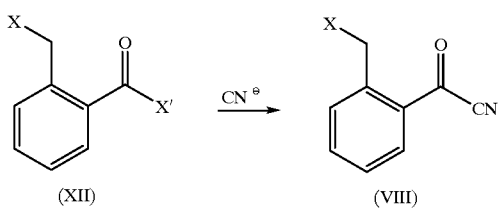

(XII)  (VIII)

wherein X' is as define as X, and the other symbols are as defined above.

The compound (VIII) can be prepared by reacting the compound (XII) with a cyanide ion in an appropriate solvent (see T. S. Oakwood, C. A. Weisgerber, Org. Synth. III, 112 (1955)).

The cyanide ion is normally used as a metal cyanide (e.g., cuprous cyanide, sodium cyanide, potassium cyanide, lithium cyanide, etc.) for this reaction. The amount of the metal cyanide to be used is 1 to 5 mol, preferably 1 to 1.5 mol, per mol of the compound (XII).

The solvents include, for example, nitrites (e.g., acetonitrile, etc.), amides (e.g., N,N-dimethylformamide, etc.), hydrocarbons (e.g., toluene, etc.), etc. In particular, acetonitrile is preferred.

If necessary, this reaction may be carried out in the presence of a catalyst. The catalysts include, for example, metal halides (e.g., copper iodide, copper bromide, copper chloride, etc.), organic bases (e.g., quinoline, pyridine, 4-dimethylaminopyridine, etc.), etc. The amount of the catalyst to be used is 0.01 to 1 mol, preferably 0.01 to 0.2 mol, per mol of the compound (XII).

The reaction temperature is normally 20 to 100° C., preferably 40 to 80° C., and the reaction time is normally 2 to 20 hours.

The compound (VIII) thus obtained can be used in the next step as the reaction mixture or crude product, or after purifying it by conventional methods (e.g., chromatography, recrystallization, etc.).

The starting compound (XII) for this reaction can be obtained, for example, by reacting phthalide with a triphenylphosphine halogenide according to D. J. Burton, W. M. Koppes, J. Chem. Soc. Chem. Commun. 425 (1973).

The compound of the formula (I-2) obtained by the reaction of Scheme 3 or 4 can conveniently be converted into the compound (IX) having potent fungicidal activity useful as an agricultural fungicide, for example, according to Scheme 13 (see JP-A 3-246268). The compound (I-2) is thus useful as an intermediate for the production of the compound (IX).

Scheme 13

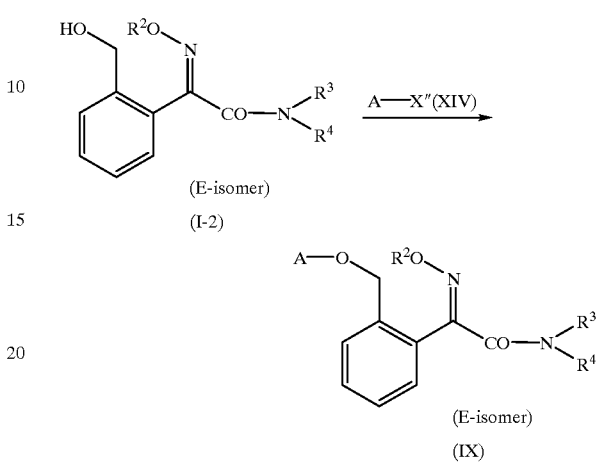

(E-isomer)
(I-2)

(E-isomer)
(IX)

wherein A is an optionally substituted phenyl group or an optionally substituted heterocyclic group, X" is as defined as X, and the other symbols are as defined above.

That is, the compound (I-2) can be reacted with the compound (XIV) according to JP-A 3-246268 to give the compound (IX).

The optionally substituted phenyl groups represented by A includes unsubstituted and substituted phenyl groups. The substituents of the substituted phenyl groups are selected from the substituents of the phenyl group of the above substituted phenylalkyl groups represented by $R^1$. The substituted phenyl group represented by A is preferably 2,5-dimethylphenyl.

The optionally substituted heterocyclic groups represented by A include, for example, heterocyclic groups containing at least one ring-constituting heteroatom selected from nitrogen, oxygen and sulfur. Examples of the heterocyclic groups include pyridyl, pyrimidinyl, oxazolyl, thiazolyl, pyrazolyl, imidazolyl, isoxazolyl, isothiazolyl, quinolyl, etc. When the heterocyclic group is substituted, the substituent is selected from the substituents of the phenyl group of the above substituted phenylalkyl groups represented by $R^1$. The substituent is preferably a lower alkyl group, a halogenated lower alkyl group, a halogen atom, or an alkoxy group, more preferably methyl, trifluoromethyl, trichloromethyl, a fluorine atom, a chlorine atom, or methoxy.

The compound (I-2) can also be converted into the compound (IX) according to Scheme 14 or 15 below.

Scheme 14

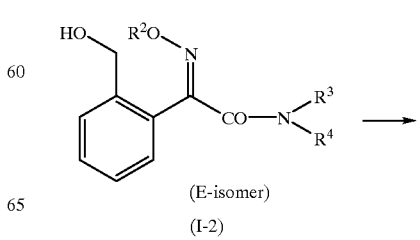

(E-isomer)
(I-2)

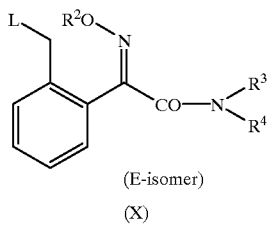

(E-isomer)

(X)

wherein L is halogen, an optionally substituted alkylsulfonyloxy group or an optionally substituted arylsulfonyloxy group, and the other symbols are as defined above.

That is, the hydroxyl group of the compound (I-2) is converted into halogen, an optionally substituted alkylsulfonyloxy group or an optionally substituted arylsulfonyloxy group to produce the compound (X).

The halogen represented by L include, for example, chlorine, bromine, iodine, etc.

The optionally substituted alkylsulfonyloxy groups represented by L include, for example, methanesulfonyloxy, trifluoromethanesulfonyloxy, etc.

The optionally substituted arylsulfonyloxy groups represented by L include, for example, p-toluenesulfonyloxy, 4-bromophenylsulfonyloxy, benzenesulfonyloxy, etc.

The conversion into the halogen can normally be carried out by reacting the compound (I-2) with a halogenating agent. The halogenating agents include, for example, thionyl halides (e.g., thionyl chloride, thionyl bromide, etc.), phosphoryl halides (e.g., phosphoryl chloride, phosphoryl bromide, etc.), tetrahalogenomethanes (e.g., carbon tetrachloride, carbon tetrabromide, etc.) in the presence of organic phosphorus compounds (e.g., triphenylphosphine, etc.), etc. The amount of the halogenating agent to be used is 1 to 5 mol, preferably 1 to 2 mol, per mol of the compound (I-2).

When the halogenating agent is used, this reaction is carried out in the absence of any solvent or in an appropriate solvent, if necessary, in the presence of a phase-transfer catalyst. The organic solvents include, for example, hydrocarbons (e.g. toluene, benzene, etc.), halogenated hydrocarbons (e.g., dichloromethane, chloroform, 1,2-dichloroethane, chlorobenzene, etc.), ethers (e.g., diethyl ether, tetrahydrofuran, dioxane, etc.), etc. These organic solvents can be used alone or as mixture thereof. The phase-transfer catalysts include, for example, quaternary ammonium salts [e.g., tetraalkylammonium halides (e.g., tetrabutylammonium chloride, tetrabutylammonium bromide, etc.), -tetraalkylammonium hydrosulfates (e.g., tetrabutylammonium hydrosulfate, etc.), etc.], amines (e.g., tris(3.6-dioxaheptyl)amine, etc.), etc. The amount of the phase-transfer catalyst to be used is 0.01 to 1 mol, preferably 0.05 to 0.5 mol, per mol of the compound (I-2).

The reaction temperature for the halogenation is normally −20 to 150° C., preferably 0 to 100° C., and the reaction time is generally 0.5 to 2 hours.

The conversion into the optionally substituted alkylsulfonyloxy group or the optionally substituted arylsulfonyloxy group is carried out by reacting the compound (I-2) with e.g. an optionally substituted alkylsulfonyl halide (e.g., methanesulfonyl chloride, trifluoromethanesulfonyl chloride, etc.) or an optionally substituted arylsulfonyl halide (e.g., p-toluenesulfonyl chloride, benzenesulfonyl chloride, 4-bromophenylsulfonyl chloride, etc.), etc. The amounts of these compounds to be used are 1 to 5 mol, preferably 1.0 to 1.5 mol, per mol of the compound (I-2).

When the arylsulfonyl halide or the alkylsulfonyl halide is used, this reaction is carried out in an appropriate organic solvent in the presence of a base. The organic solvent is selected from the organic solvents used in the above reaction using a halogenating agent. The bases include, for example, amines (e.g., pyridine, triethylamine, etc.), etc.

The reaction temperature for the conversion into the arylsulfonyloxy or alkylsulfonyloxy is normally −20 to 100° C., preferably −20 to 20° C., and the reaction time is normally 0.5 to 2 hours.

The compound (X) thus obtained can be used in the next step as the reaction mixture or crude product, or after purifying it by conventional methods (e.g., chromatography, recrystallization, etc.).

The compound (X) can be converted into the compound (IX) according to Scheme 15 below.

Scheme 15

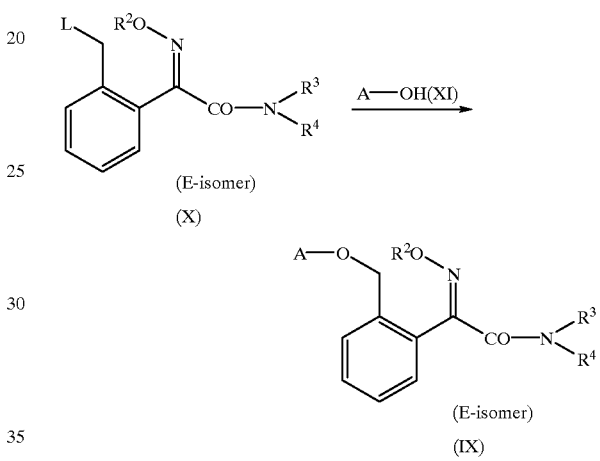

(E-isomer)

(X)

(E-isomer)

(IX)

wherein each symbol is as defined above.

That is, the compound (IX) can be prepared by reacting the compound (X) with the compound (XI) in an appropriate organic solvent in the presence of a base. The amount of the compound (XI) to be used is 1 to 10 mol, preferably 1 to 3 mol, per mol of the compound (X).

The organic solvents include, for example, ketones (e.g., acetone, ethyl methyl ketone, etc.), nitriles (e.g., acetonitrile, etc.), ethers (e.g., dioxane, tetrahydrofuran, etc.), amides (e.g., N,N-dimethylformamide, etc.), hydrocarbons (e.g., toluene, benzene, etc.), sulfoxides (e.g., dimethyl sulfoxide, etc.), etc. These organic solvents can be used alone or as mixtures thereof.

The bases include, for example, alkaline metal carbonates (e.g., sodium carbonate, potassium carbonate, etc.), alkaline metal hydroxides (e.g., sodium hydroxide, potassium hydroxide, etc.), metal hydrides (e.g., sodium hydride, etc.), etc. The amount of the compound (X) to be used is 1 to 10 mol, preferably 1 to 3 mol, per mol of the compound (X).

If necessary, this reaction may be carried out in the presence of a phase-transfer catalyst or metal halide. The phase-transfer catalysts include, for example, quaternary ammonium salts [e.g., tetraalkylammonium halides (e.g., tetrabutylammonium chloride, tetrabutylammonium bromide, etc.), tetraalkylammonium hydrosulfates (e.g., tetrabutylammonium hydrosulfate, etc.), etc.], amines (e.g., tris(3,6-dioxaheptyl)amine, etc.), etc. The amount of the phase-transfer catalyst to be used is 0.01 to 1 mol, preferably 0.05 to 0.5 mol, per mol of the compound (X). The metal halides include, for example, potassium iodide, sodium iodide, sodium bromide, potassium bromide, etc. The amount of the metal halide to be used is 0.01 to 5 mol, preferably 0.1 to 2 mol, per mol of the compound (X).

As disclosed in JP-A 3-246268 and JP-A 4-182461, the compound (IX) obtained in the reaction of above Scheme 13 or 15 has potent fungicidal activity, and can be used as an agricultural fungicide.

EXAMPLES

The following examples and reference examples further illustrate the present invention in detail, but are not to be construed to limit the scope thereof.

Example 1

Synthesis of 2-(2-chloromethylphenyl)-2-oxoacetonitrile—(1)

A mixture of acetonitrile (100 ml), 95% sodium cyanide (6.19 g), 95% cuprous iodide (2.00 g) and quinoline (0.13 g) was stirred at 60° C. A solution of 2-chloromethylbenzoyl chloride (19.0 g) in acetonitrile (100 ml) was added dropwise to the reaction mixture over 3 hours. After completion of the addition, the mixture was stirred at 60° C. for 5 hours. After the reaction mixture was cooled by allowing it to stand, the reaction mixture was diluted with ether, and washed successively with water, a saturated aqueous solution of sodium bicarbonate and water. The ether layer thus obtained was dried over anhydrous sodium sulfate and at the same time decolorized with Norit SX-3. Evaporation of the solvent under reduced pressure gave the crude title compound (17.6 g, purity: about 72% determined by $^1$H-NMR analysis).

The 2-chloromethylbenzoyl cyanide was normally used in the next step as the crude product. If necessary, it was isolated as white crystals by crystallizing it from ether-hexane.

mp. 54.5–56.6° C.
$^1$H-NMR (CDCl$_3$) δ ppm: 5.00(2H,s), 7.62–7.84(3H,m), 8.35(1H,dd,J=7.9,1.2 Hz).

Example 2

Synthesis of 2-(2-chloromethylphenyl)-2-oxoacetonitrile—(2)

A mixture of 98% cuprous cyanide (2.01 g), acetonitrile (40 ml) and 2-chloromethylbenzoyl chloride (3.79 g) was heated under reflux with stirring for 4 hours. After the mixture was cooled by allowing it to stand, the mixture was diluted with ether, the precipitated insoluble materials were filtered off, and then the filtrate was washed successively with a saturated aqueous solution of sodium bicarbonate, water and saturated brine. The ether layer thus obtained was dried over anhydrous sodium sulfate, and then the solvent was evaporated under reduced pressure to obtain the crude product (3.49 g). The crude product was crystallized from ether-haxane to give the title compound (2.85 g, yield: 79.5%, white crystals).

mp. 54.5–56.5° C.
$^1$H-NMR (CDCl$_3$) δ ppm: 5.00(2H,s), 7.62–7.84(3H,m), 8.35(1H,dd,J=7.9,1.2 Hz).

Example 3

Synthesis of 2-(2-chloromethylphenyl)-2-oxoacetamide—(1)

Crude 2-(2-chloromethylphenyl)-2-oxoacetonitrile (purity: about 72%)(17.6 g), water (1.76 g) and 5N hydrogen chloride/dioxane solution (200 ml) were added into a round-bottom flask. The flask was stoppered, and then the mixture was stirred at room temperature for 3 days. After the reaction mixture was ice-cooled, water (150 ml) was added, and the mixture was stirred at room temperature for 40 minutes. The reaction mixture was diluted with ethyl acetate, and washed successively with a saturated aqueous solution of sodium bicarbonate, water and saturated brine. The ethyl acetate layer obtained was dried over anhydrous sodium sulfate and at the same time decolorized with Norit SX-3. Evaporation of the solvent under reduced pressure gave the crude product (16.6 g). The crude product was crystallized from ethyl acetate-hexane, and the crystallization mother liquor was purified by column chromatography on silica gel to obtain the title compound (11.3 g, total yield in the two steps: 57.3%, pale yellow crystals).

mp. 114–115° C.
$^1$H-NMR (CDCl$_3$) δ ppm: 4.88(2H,s), 5.84(1H,br-s), 6.99 (1H,br-s), 7.42–7.62(3H,m), 8.01(1H,d,J=7.9 Hz).

Example 4

Synthesis of 2-(2-chloromethylphenyl)-2-oxoacetamide—(2)

A mixture of 2-(2-chloromethylphenyl)-2-oxoacetonitrile (1.80 g) and 36% hydrochloric acid aqueous solution (10 ml) was stirred at 40° C. for 20 hours. After the mixture was cooled by allowing it to stand, ice-cooled water was added, and the resulting mixture was stirred at room temperature for 30 minutes. The mixture was extracted with ethyl acetate twice. The combined ethyl acetate layer was washed successively with a saturated aqueous solution of sodium bicarbonate and saturated brine, and dried over anhydrous sodium sulfate. Evaporation of the solvent under reduced pressure gave a crude product (0.89 g). The crude product was recrystallized from ethyl acetate-hexane to give the title compound (0.80 g, yield: 40.2%, pale yellow crystals).

mp. 114–115° C.
$^1$H-NMR (CDCl$_3$) δ ppm: 4.88(2H,s), 5.84(1H,br-s), 6.99 (1H,br-s), 7.42–7.62(3H,m), 8.01(1H,d,J=7.9 Hz).

Example 5

Synthesis of 2-(2-acetoxymethylphenyl)-2-oxoacetamide

A mixture of 2-(2-chloromethylphenyl)-2-oxoacetamide (3.41 g), potassium acetate (2.03 g), potassium iodide (0.14 g) and N,N-dimethylformamide (35 ml) was stirred at room temperature for 24 hours. To the reaction mixture was added a mixed solution (about 300 ml) of ethyl acetate and ether in a mixing ratio of about 1:1. The mixture was washed with water twice and saturated brine once. The resulting organic layer was dried over anhydrous sodium sulfate, and the solvent was evaporated under reduced pressure to obtain the crude product (3.55 g). The crude product was recrystallized from ethyl acetate-hexane, the resulting mother liquor was concentrated under reduced pressure, and the residue was purified by column chromatography on silica gel (ethyl acetate:hexane=1:2) to give the title compound (2.62 g in total, yield: 68.6%, white crystals).

mp. 86.5–88° C.
$^1$H-NMR (CDCl$_3$) δ ppm: 2.09 ppm(3H,s), 5.37 ppm(2H, s), 5.65 ppm(1H,br-s), 6.96 ppm(1H,br-s), 7.41–7.62 ppm (3H,m), 8.00(1H,dd,J=7.4,1.2 Hz).

Example 6

Synthesis of 2-(2-acetoxymethylphenyl)-2-hydroxyiminoacetamide

A mixture of 2-(2-acetoxymethylphenyl)-2-oxoacetamide (1.56 g), 95% hydroxylamine hydrochloride (0.62 g), potassium acetate (1.34 g) and methanol (14 ml) was heated under reflux with stirring for 18 hours. After the mixture was cooled by allowing it to stand, water (about 150 ml) was added to the reaction mixture, and the mixture was extracted with ethyl acetate three times. The combined ethyl acetate layer was washed with saturated brine and dried over anhydrous sodium sulfate. Evaporation of the solvent under reduced pressure gave the crude product (1.55 g). The crude product was purified by column chromatography on silica gel (ethyl acetate:hexane=2:1) to give the title compound (1.18 g, yield: 70.9%) as a mixture of the E- and Z-isomers (E:Z=65:35 determined by $^1$H-NMR analysis).

E-isomer:

$^1$H-NMR (CDCl$_3$) δ ppm: 2.05(3H,s), 5.03(2H,s), 5.70 (1H,br-s), 6.77(1H,br-s), 7.22(1H,m), 7.38–7.49(3H,m), 9.02(1H,br-s).

Z-isomer:

$^1$H-NMR (CDCl$_3$) δ ppm: 2.06(3H,s), 5.19(2H,s), 6.14 (1H,br-s), 6.44(1H,br-s), 7.38–7.48(4H,m).

Example 7

Synthesis of (E)-2-(2-acetoxymethylphenyl)-2-hydroxyiminoacetamide

A mixture of 2-(2-acetoxymethylphenyl)-2-hydroxyiminoacetamide (388 mg, E/Z=35/65) was dissolved in a 5N hydrogen chloride/dioxane solution (3.3 ml), and the mixture was stirred at room temperature for 2.5 hours. The reaction mixture was poured into an ice-cooled saturated aqueous solution of sodium bicarbonate, and extracted with ethyl acetate three times. The combined ethyl acetate layer was washed successively with water and saturated brine, and dried over anhydrous sodium sulfate. Evaporation of the solvent under reduced pressure gave the crude product (300 mg). This crude product was crystallized from ethyl acetate-hexane, and the crystallization mother liquor was concentrated under reduced pressure and purified by silica gel thin layer chromatography (ethyl acetate:hexane=4:1) to obtain the title compound (243 mg in total, yield: 62.8%, pale yellow crystals).

mp. 112.5–113.5° C.

$^1$H-NMR (CDCl$_3$) δ ppm: 2.05(3H,s), 5.03(2H,s), 5.70 (1H,br-s), 6.77(1H,br-s), 7.22(1H,m), 7.38–7.49(3H,m), 9.02(1H,br-s).

Example 8

Synthesis of (E)-2-(2-acetoxymethylphenyl)-2-methoxyiminoacetamide—(1)

A mixture of (E)-2-(2-acetoxymethylphenyl)-2-hydroxyiminoacetamide (428 mg), potassium carbonate (301 mg) and acetone (3.6 ml) was stirred at room temperature. To the mixture was added dropwise 95% dimethyl sulfate (0.20 ml). The mixture was stirred at room temperature for 4.5 hours. Water (10 ml) was added to the reaction mixture, and the mixture was stirred at room temperature for 30 minutes. Water (30 ml) was added, and the mixture was extracted with ethyl acetate three times. The combined ethyl acetate layer was washed with saturated brine and dried over anhydrous sodium sulfate. Evaporation of the solvent under reduced pressure gave the crude product (440 mg). The crude product was crystallized from ethyl acetate-hexane, the crystallization mother liquor was concentrated and purified by silica gel thin layer chromatography (ethyl acetate:hexane=4:1) to obtain the title compound (432 mg in total, yield 95.6%, colorless crystals).

mp. 121.0–123.0° C.

$^1$H-NMR (CDCl$_3$) δ ppm: 2.05(3H,s), 3.99(3H,s), 4.98 (2H,s), 5.37(1H,br-s), 6.76(1H,br-s), 7.19(1H,m), 7.36–7.49 (3H,m).

Example 9

Synthesis of 2-(2-hydroxymethylphenyl)-2-methoxyimino-N-methylacetamide

A mixture of (E)-2-(2-acetoxymethylphenyl)-2-methoxyiminoacetamide (432 mg), 40% methylamine/methanol solution (5 ml) and methanol (5 ml) was stirred at 60° C. for 16 hours in a sealed tube. After the mixture was cooled by allowing it to stand, the solvent was evaporated under reduced pressure. The resulting residue was crystallized from ethyl acetate-hexane. The crystallization mother liquor was concentrated under reduced pressure and purified by column chromatography on silica gel (ethyl acetate:hexane=4:1) to obtain the title compound (379 mg, yield: 98.3%, white crystals) as a mixture of the E- and Z-isomers (E/Z≠93/7 determined by $^1$H-NMR analysis).

E-isomer:

mp. 100–102° C.

$^1$H-NMR (CDCl$_3$) δ ppm: 2.95(3H,d,J=4.9 Hz), 3.10 (1H,t,J=6.7 Hz), 3.96(3H,s), 4.40(2H,d,J=6.7 Hz), 6.93(1H, br-s), 7.13(1H,dd,J=7.9,1.2 Hz), 7.35(1H,td,J=7.9,1.2 Hz), 7.43 (1H,td,J=7.9,1.2 Hz), 7.51(1H,dd,J=7.9,1.2 Hz).

Example 10

Synthesis of 2-(2-acetoxymethylphenyl)-2-methoxyiminoacetamide

A mixture of 2-(2-acetoxymethylphenyl)-2-oxoacetamide (776 mg), O-methylhydroxylamine hydrochloride (439 mg), toluene (7.0 ml) and pyridine (3.5 ml) was stirred at 80° C. for 2 hours. After the reaction mixture was cooled by allowing it to stand, the reaction mixture was diluted with ethyl acetate, washed successively with 1N hydrochloric acid, water, saturated brine, and dried over anhydrous sodium sulfate. Evaporation of the solvent under reduced pressure gave the crude product (830 mg). This crude product was purified by column chromatography on silica gel to obtain the title compound (793 mg, yield: 90.3%, pale yellow crystals) as a mixture of the E- and Z-isomers (E/Z=56/44 determined by $^1$H-NMR analysis).

E-isomer:

$^1$H-NMR (CDCl$_3$) δ ppm: 2.05(3H,s), 3.99(3H,s), 4.98 (2H,s), 5.37(1H,br-s), 6.76(1H,br-s), 7.19(1H,m), 7.36–7.49 (3H,m).

Z-isomer:

$^1$H-NMR (CDCl$_3$) δ ppm: 2.06(3H,s), 4.06(3H,s), 5.27 (2H,s), 6.07(1H,br-s), 6.94(1H,br-s), 7.32–7.50(4H,m).

Example 11

Synthesis of (E)-2-(2-acetoxymethylphenyl)-2-methoxyiminoacetamide—(2)

A mixture of 2-(2-acetoxymethylphenyl)-2-methoxyiminoacetamide (793 mg, E/Z=56/44) was dissolved in a 6N hydrogen chloride/dioxane solution (6.3 ml), and the mixture was stirred at room temperature for 3 hours. The reaction mixture was poured into an ice-cooled saturated aqueous solution of sodium bicarbonate, and extracted with ethyl acetate twice. The combined ethyl acetate layer was washed successively with water and saturated brine, and dried over anhydrous sodium sulfate. Evaporation of the solvent under reduced pressure gave the crude product (700 mg). This crude product was crystallized from ethyl acetate-hexane. The crystallization mother liquor was concentrated under reduced pressure and purified by column chromatography on silica gel (ethyl acetate:hexane=1:1) to obtain the title compound (616 mg in total, yield: 77.6%, pale yellow crystals).

mp. 121.0–123.0° C.

$^1$H-NMR (CDCl$_3$) δ ppm: 2.05(3H,s), 3.99(3H,s), 4.98 (2H,s), 5.37(1H,br-s), 6.76(1H,br-s), 7.19(1H,m), 7.36–7.49 (3H,m).

Example 12

Synthesis of 2-(2-hydroxymethylphenyl)-2-methoxyimino-N-methylacetamide

A mixture of 2-(2-acetoxymethylphenyl)-2-hydroxyiminoacetamide (945 mg, E/Z≠65/35), a 40% methylamine/methanol solution (2.0 ml) and methanol (6.0 ml) was stirred at 40° C. for 4 hours. After the mixture was cooled by allowing it to stand, the solvent was evaporated under reduced pressure. The residue was dissolved in acetone (8.0 ml). 95% Dimethyl sulfate (1.17 g) and potassium carbonate (1.33 g) were added, and the mixture was stirred at room temperature for 7 hours. A small quantity of ice piece was added, and the mixture was stirred for 20 minutes. The reaction mixture was poured into water (about 100 ml), and the mixture was extracted with ethyl acetate three times. The combined ethyl acetate layer was washed with saturated brine, dried over anhydrous sodium salfate, and the solvent was evaporated under reduced pressure. The resulting residue was purified by column chromatography on silica gel (ethyl acetate/hexane=2/1) to obtain the title compound (563 mg, E/Z≠98/2, yield: 63.3%). This compound was crystallized from ethyl acetate-hexane to obtain the title compound as crystals (420 mg, E/Z=98/2).

mp. 103–105° C.

$^1$H-NMR (CDCl$_3$) δ ppm: 2.95(3×(98/100)H,d,J=4.9 Hz), 2.98(3×(2/100)H,d,J=4.9 Hz), 3.96(3×(98/100)H,s), 4.06 (3× (2/100)H,s), 4.40(2×(98/100)H,s), 4.59(2×(2/100)H,s), 6.95 (1H,br-s), 7.13(1H,dd,J=7.3,1.2 Hz), 7.35(1H,td,J=7.3, 1.2 Hz), 7.43(1H,td,J=7.3,1.2 Hz), 7.53(1H,dd,J=7.3,1.2 Hz).

Example 13

Synthesis of 2-(2-hydroxymethylphenyl)-2-methoxyimino-N-methylacetamide

A mixture of 2-(2-hydroxymethylphenyl)-2-hydroxyimino-N-methylacetamide (521 mg, E/Z≠93/7), potassium carbonate (415 mg), 95% dimethyl sulfate (365 mg) and acetone (5.0 ml) was stirred at room temperature for 6 hours. A few pieces of ice were added, and the mixture was stirred for 30 minutes. Water (about 50 ml) was added, and the mixture was extracted with ethyl acetate three times. The combined ethyl acetate layer was washed with saturated brine and dried over anhydrous sodium sulfate. Evaporation of the solvent under reduced pressure gave the crude product (E/Z≠9 97/3). The crude product was crystallized from ethyl acetate-hexane to obtain the title compound as crystals (389 mg) (E/Z=97/3, yield: 70.0%).

Example 14

Synthesis of 2-(2-hydroxymethylphenyl)-2-hydroxyimino-N-methylacetamide

A mixture of 2-(2-acetoxymethylphenyl)-2-hydroxyiminoacetamide (1.00 g, E/Z≠65/35), a 40% methylamine/methanol solution (2.1 ml) and methanol (6.3 ml) was stirred at 40° C. for 6 hours. After the mixture was cooled by allowing it to stand, the solvent was evaporated under reduced pressure to obtain the crude product (E/Z≠98/ 2). This crude product was purified by column chromatography on silica gel (ethyl acetate) and crystallized from ethyl acetate-hexane to obtain the title compound as crystals (594 mg, E/Z≠93/7, yield: 67.4%).

mp. 128–131° C.

$^1$H-NMR (CDCl$_3$) δ ppm: 2.93(3H,d,J=4.9 Hz), 4.43(2× (93/100)H,s), 4.60(2×(7/100)H,s), 6.93(1H,br-s), 7.17(1H, dd,J=7.3,1.2 Hz), 7.38(1H,td,J=7.3,1.2 Hz), 7.45(1H,td,J= 7.3,1.2 Hz),7.54(1H,dd,J=7.3,1.2 Hz),8.42(1H,br-s).

Example 15

Synthesis of 2-(2-acetoxymethylphenyl)-2-methoxyiminoacetamide

A mixture of 2-(2-acetoxymethylphenyl)-2-hydroxyiminoacetamide (253 mg, E/Z≠65/35), potassium carbonate (177 mg), 95% dimethyl sulfate (148 mg) and acetone (4.0 ml) was stirred at room temperature for 4 hours. A few pieces of ice were added, and the mixture was stirred for 20 minutes. The reaction mixture was diluted with ethyl acetate, washed successively with water and saturated brine, and dried over anhydrous sodium sulfate. Evaporation of the solvent under reduced pressure gave the crude product. The crude product was purified by column chromatography on silica gel (ethyl acetate/hexane=2/1) to obtain the title compound (194 mg, E/Z≠79/21, yield: 72.4%).

Example 16

Synthesis of 2-(2-hydroxymethylphenyl)-2-methoxyimino-N-methylacetamide

A mixture of 2-(2-acetoxymethylphenyl)-2-methoxyiminoacetamide (194 mg, E/Z≠79/21), methanol (3.0 ml) and a 40% methylamine/methanol solution (1.0 ml) was stirred at 40° C. for 3 hours. After the mixture was ice-cooled, the solvent was evaporated under reduced pressure to obtain the crude product (203 mg, E/Z≠91/9) of the title compound.

Reference Example 1

Synthesis of (E)-2-(2-chloromethylphenyl)-2-methoxyimino-N-methylacetamide

Thionyl chloride (3.0 ml) was added to a mixture of 2-(2-hydroxymethylphenyl)-2-methoxyimino-N-methylacetamide (3.0 g), tetrabutylammonium chloride (380 mg) and toluene (30 ml) at room temperature. The mixture was stirred for 10 minutes, and then stirred at 60° C. for 1.5 hours. After the mixture was cooled by allowing it to stand, the solvent was evaporated under reduced pressure. The residue was dissolved in diethyl ether, and washed successively with water and saturated brine. The ether layer was dried over anhydrous sodium sulfate, the solvent was evaporated under reduced pressure, and the resulting residue was dissolved in a small amount of diethyl ether. Hexane was added to the solution to obtain the title compound as crystals (2.6 g, 80%).

mp. 72–74° C.

$^1$H-NMR (CDCl$_3$) δ ppm: 2.95(3H,d,J=5.2 Hz), 3.98 ppm(3H,s), 4.46(2H,s), 6.80(1H,br), 7.18(1H,m), 7.35–7.45 (2H,m), 7.50(1H,m).

$^{13}$C-NMR (CDCl$_3$) δ ppm: 26.11(q), 44.12(t), 63.19(q), 128.02(d), 128.86(d), 129.37(d), 129.52(d), 129.65(s), 135.57(s), 150.44(s), 162.62(s).

Reference Example 2

Synthesis of (E)-2-methoxyimino-2-(2-(2,5-dimethylphenoxymethyl)phenyl)-N-methylacetamide—(1)

A mixture of (E)-2-(2-chloromethylphenyl)-2-methoxyimino-N-methylacetamide (500 mg), 2,5-dimethylphenol (700 mg), potassium carbonate (700 mg), potassium iodide (500 mg) and acetone (5.0 ml) was heated under reflux with stirring for 6 hours. After the mixture was cooled by allowing it to stand, ethyl acetate was added to the reaction mixture. The mixture was washed successively with water and saturated brine. The organic layer was dried over anhydrous sodium sulfate. The solvent was evaporated under reduced pressure. The resulting residue was subjected to column chromatography on silica gel (ethyl acetate:hexane=2:1) to obtain the title compound (530 mg, 78%). This compound was crystallized from diethyl ether-hexane to obtain the title compound as crystals (430 mg, 63%).

mp. 135–138° C.

In a similar manner, (E)-2-methoxyimino-2-(2-(4-methylphenoxymethyl)phenyl)-N-methylacetamide was obtained as crystals (yield: 68%).

mp. 130–132° C.

Reference Example 3

Synthesis of (E)-2-methoxyimino-2-(2-(2,5-dimethylphenoxymethyl)phenyl)-N-methylacetamide—(2)

A mixture of (E)-2-(2-chloromethylphenyl)-2-methoxyimino-N-methylacetamide (500 mg), 2,5-dimethylphenol (700 mg), potassium carbonate (700 mg) and acetone (5.0 ml) was stirred in a sealed tube at 60° C. for 45 hours. After the mixture was cooled by allowing it to stand, ethyl acetate was added thereto. The mixture was washed successively with water and saturated brine. The organic layer was dried over anhydrous sodium sulfate and concentrated to dryness under reduced pressure. The resulting residue was subjected to column chromatography on silica gel (ethyl acetate:hexane=1:2) to obtain the title compound (360 mg, 53%). In this chromatographic separation, some of the starting compound was recovered.

Reference Example 4

(E)-2-[2-(5-chloro-3-trifluoromethylpyridin-2-yloxymethyl)phenyl]-2-methoxyimino-N-methylacetamide 2-(2-Hydroxymethylphenyl)-2-methoxyimino-N-methylacetamide (300 mg) was dissolved in THF (5 ml). 60% Sodium hydride (65 mg) was added, and the mixture was stirred for 10 minutes. 2,5-Dichloro-3-trifluoromethylpyridine (350 mg) was added, and the mixture was stirred at room temperature for 12 hours, neutralized with 1N-hydrochloric acid and extracted with ethyl acetate. The organic layer was dried over MgSO$_4$, and the solvent was evaporated under reduced pressure. The resulting residue was purified by column chromatography on silica gel to obtain the title compound (398 mg, yield: 74%).

mp. 105–106° C.

$^1$H-NMR (CDCl$_3$) δ ppm: 2.94(3H,d,J=5.1Hz), 3.96 (3H, s), 5.23(2H,s), 6.82(1H,brs), 7.21(1H,dd,J=7.3,1.7 Hz), 7.36 (1H,td,J=7.3,1.7 Hz), 7.42(1H,td,J=7.3,1.7 Hz), 7.58(1H,dd, J=7.3,1.7 Hz), 7.81(IH,dd,J=2.4,0.7 Hz), 8.16(1H,dd,J=2.4, 0.7 Hz).

The present invention provides a safe and industrially advantageous process for producing an alkoxy(or hydroxy) iminoacetamide derivative useful as an intermediate for the production of alkoxyiminoacetamide compounds useful as agricultural fungicides. The present invention also provides intermediates for the production.

The process of the present invention providing the compound (I) from the compound (II) is characterized in that an amine is used for amino-exchange reaction. When a monomethyl (—NHCH$_3$) compound is desired, the prior art methods (e.g., alkylation with an alkylating agent such as dimethyl sulfate, methyl chloride, etc.) produce a mixture of the desired monomethyl (—NHCH$_3$) compound, an unreacted (—NH$_2$) compound and a dimethyl (—N(CH$_3$)$_2$) compound, and thus cannot selectively produce only the desired compound. However, the process of the invention selectively produces a monomethyl compound when it is desired, and a dimethyl compound when it is desired.

The alkoxyiminoacetamide compound that is obtainable from the compound (I) through a few steps and useful as an agricultural fungicide has superior fungicidal activity when it is its E-isomer. Therefore it is preferred to obtain the compound (I) as its E-isomer. In the process of the invention, the above amino-exchange reaction and the isomerization to the E-isomer proceed at the same time. Thus, the process of the invention produces the compound (I) in a high yield through a few reaction steps not including a separate isomerization step to the E-isomer, and is very advantageous for the industrial production.

We claim:

1. A process for producing a compound of the formula (I):

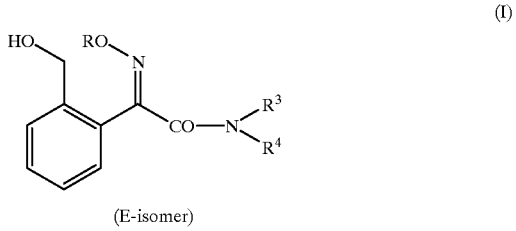

(E-isomer)

wherein R is hydrogen or an alkyl group, and R$^3$ and R$^4$ are the same or different and are hydrogen or an alkyl group, which comprises reacting a compound of the formula (II):

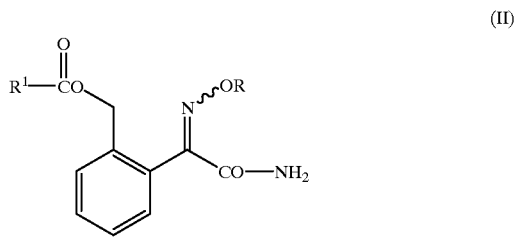

wherein R$^1$ is an optionally substituted alkyl group or an optionally substituted phenyl group, ~ indicates any configuration of an E-isomer, a Z-isomer and a mixture thereof, and the other symbols are as defined above, with a compound of the formula (III):

HNR³R⁴ (III)

wherein each symbol is as defined above; wherein, in the process, isomerization takes place in the absence of an acid.

2. A process for producing a compound of the formula (I-2):

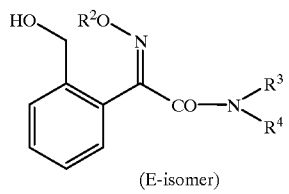

(I-2)

(E-isomer)

wherein $R^2$ is an alkyl group, and $R^3$ and $R^4$ are the same or different and are hydrogen or an alkyl group, which comprises reacting a compound of the formula (II-1):

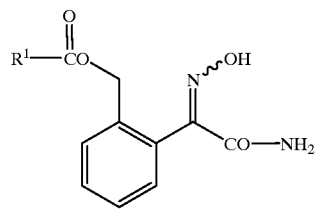

(II-1)

wherein $R^1$ is an optionally substituted alkyl group or an optionally substituted phenyl group, ~ indicates any configuration of an E-isomer, a Z-isomer and a mixture thereof, and the other symbols are as defined above, with a compound of the formula (III):

HNR³R⁴ (III)

wherein each symbol is as defined above to obtain a compound of the formula (I-1):

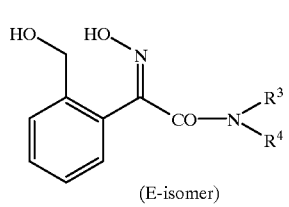

(I-1)

(E-isomer)

wherein each symbol is as defined above, and then alkylating the compound of the formula (I-1); wherein, in the process, the isomerization takes place in the absence of an acid.

3. A process for producing a compound of the formula (I-2):

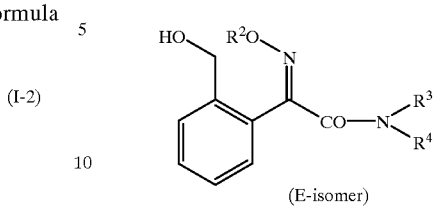

(I-2)

(E-isomer)

wherein $R^2$ is an alkyl group, and $R^3$ and $R^4$ are the same or different and are hydrogen or an alkyl group, which comprises alkylating a compound of the formula (II-1):

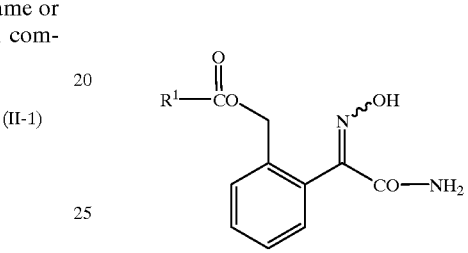

(II-1)

wherein $R^1$ is an optionally substituted alkyl group or an optionally substituted phenyl group, ~ indicates any configuration of an E-isomer, a Z-isomer and a mixture thereof, and the other symbols are as defined above, to obtain a compound of the formula (II-2):

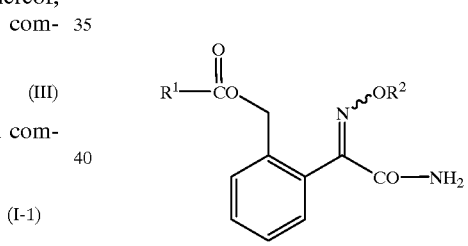

(II-2)

wherein each symbol is as defined above, and then reacting the compound of the formula (II-2) with a compound of the formula (III):

HNR³R⁴ (III)

wherein each symbol is as defined above; wherein, in the process, isomerization takes place in the absence of an acid.

* * * * *